United States Patent [19]

Ericksson et al.

[11] 4,265,927

[45] May 5, 1981

[54] METHOD OF HEPARINIZING A CHARGED SURFACE OF A MEDICAL ARTICLE INTENDED FOR BLOOD CONTACT

[75] Inventors: Jan C. Ericksson, Djursholm; Rolf L. Larsson, Ekerö, both of Sweden

[73] Assignee: Aminkemi AB, Bromma, Sweden

[21] Appl. No.: 922,992

[22] Filed: Jul. 10, 1978

[30] Foreign Application Priority Data

Jul. 18, 1977 [SE] Sweden ................................. 7708296

[51] Int. Cl.³ .............................................. A01N 43/16
[52] U.S. Cl. ....................................... 427/2; 424/183; 3/1.4
[58] Field of Search .................. 424/183; 427/2; 3/1.4

[56] References Cited

U.S. PATENT DOCUMENTS

| | | | |
|---|---|---|---|
| 3,475,358 | 10/1969 | Böxler | 424/183 |
| 3,506,642 | 4/1970 | Kolt | 424/183 |
| 3,634,123 | 1/1972 | Eriksson | 424/183 |
| 3,846,353 | 11/1974 | Grotta | 424/183 |
| 4,118,485 | 10/1978 | Eriksson | 424/183 |

*Primary Examiner*—Sam Silverberg
*Attorney, Agent, or Firm*—Brumbaugh, Graves, Donohue & Raymond

[57] ABSTRACT

A charged surface of a medical article intended for blood contact can be heparinized by being contacted with a collodial aqueous solution of a complex compound of heparin and a cationic surfactant, the particles of the collodial solution having attached to their surfaces charges of a polarity opposite to that of the charges of the article.

11 Claims, No Drawings

METHOD OF HEPARINIZING A CHARGED SURFACE OF A MEDICAL ARTICLE INTENDED FOR BLOOD CONTACT

For counteracting the thrombocyte (blood platelet) adhesion and the formation of thrombi when blood is contacted with various medical articles, such as catheters, blood oxygenators, artificial cardiac valves, blood bags, and for reducing the risk of thrombocytopenia and thrombosis, methods of attaching heparin, which is a well known anticoagulant, to the surfaces of such articles have been developed.

Several of the previously known methods for the heparinization of surfaces of medical articles are based on the formation of complex compounds of low solubility of heparin, which is chemically an alkali salt of a strongly sulphated mucopolysaccharide, and a cationic surfactant, i.e. a chemical compound of salt character with surface-active positive ion usually containing a relatively long hydrocarbon chain. When the surface to be heparinized consists of a plastics surface, e.g. polyethylene or polypropylene, the formation of the complex compound can take place while simultaneously forming a more or less fine-grained film on the plastics surface. The plastics surface is hereby treated in steps at increased temperature, first with an aqueous solution of the cationic surfactant and subsequently with an aqueous solution of heparin. It has also been proposed to attach a complex compound of heparin and a cationic surfactant to a plastics surface by contacting the plastics surface with an aqueous dispersion of the complex compound for a relatively long time at the softening temperature of the plastics with subsequent cooling. Methods of this kind have been disclosed in, for example, Swedish Pat. Nos. 306,597 and 315,362. One of the experiences from industrial heparinization according to these methods is that the result of the treatment varies with the chemical state of the surface of the plastics material, which is difficult to control beforehand. Furthermore, the grain size in the resulting heparin film, which to a great extent is decisive for the blood contact properties of the film, is heavily dependent on different process variables, such as solution temperatures and flow rates. As a result of this there are great demands on how exactly the process is carried out, as well as on quality control of the products after heparinization. These known methods also have the limitation that they are applicable only to products made from certain plastics, primarily of the polyolefin type, but not to articles made from metal or glass.

It has also been proposed to prepare the complex compound of heparin and a cationic surfactant in a separate operation, to dissolve said complex compound in an organic solvent, and to expose the surface to be heparinized to said solution. This method has been disclosed, for example in Swedish Patent Application No. 75-03240-9. This method is in principle generally applicable to various kinds of solid surfaces, because the method does not require that the surfactant is soluble in the surface zone of the solid phase.

Apart from the drawback of using organic solvents for treating medical articles, it has also been found in practice that there are often great difficulties with the method just discussed to attain complete coverage of the substrate surface with a cohesive and fine-grained film of the complex compound of sufficient thickness. The tendency to form irregular particle aggregates on the surface is often stronger than the tendency to form an evenly distributed and cohesive surface film, the result being incomplete coverage of the substrate surface, and hence, unsatisfactory blood contact properties.

Towards this background it appears important to find a new heparinization technique which can be applied with satisfactory reproducability on a variety of materials, e.g. polymeric plastics material, metals, and glass, without the necessity of using organic solvents, and which with great reliability leads to proper coverage of the substrate surface with a cohesive film consisting of a complex compound of heparin and a cationic surfactant, said film being fine-grained and having a predetermined thickness.

The solution of this problem is based on the following observations and working hypotheses:

The adsorption of a charged particle on the surface of a solid body is not only determined by the van der Waals forces between the particle and the solid body, but also by the mutual charge relationships. Thus, adsorption and adhesion to the surface is favoured when the charges, i.e. ionic groups, attached to the particle surfaces and the surface of the solid body, respectively, are of opposite polarity. In an aqueous solution of heparin there are polymeric heparinate ions having a negative charge. The counter-ions usually consist of positive sodium ions. An insoluble complex compound of heparin and a cationic surfactant can be produced in the form of colloidal particles in an aqueous solution. In such a solution the colloidal articles have positive ionic charges attached to their surfaces when the amount of cationic surfactant in relation to the amount of heparin exceeds the corresponding relative amount required for flocculation. When the amount of cationic surfactant in relation to the amount of heparin is less than the relative amount required for flocculation, the colloidal particles have instead an excess of negative ionic charges attached to their surfaces. The counter-ions, having charges of a polarity opposite to that of the attached charges, are more freely mobile within a diffuse layer in the aqueous phase nearest to the particle surface.

If the surface to be heparinized has attached ionic groups of a certain polarity, positive or negative, this encourages the adsorption on said surface of colloidal particles of a complex compound of heparin and a cationic surfactant, said colloidal particles having on their surface attached ionic charges of opposite polarity. This is in particular so when the colloidal particles are of a comparatively small size.

Articles considered for heparinization are usually manufactured from plastics or metal. Provided that they are well cleaned, there occurs at many such surfaces in contact with water a so-called electrical double layer, consisting of ionic charges attached to the surface and mobile counter-ions in the water layer closest to the surface. This is usually the case for airoxidized metallic surfaces, for example. When a surface has insufficient charge density, which is often the case for certain plastics surfaces, a higher charge density can usually be created in a method known per se. One known method comprises treating the surface with an oxidant or a strong acid or both, cf. Swedish Patent Application No. 77-06746-0. Another known method comprises making the surface adsorb a layer of a surfactant or a protein.

Surfaces with a relatively high charge density most often have a good wettability. Therefore, a wettability test is often sufficient to determine the charge density of the surface. Such surfaces which have attached ionic charges to a relatively high density are called "charged surfaces" in the following specification and claims.

When a charged surface is brought into contact with a colloidal solution of particles having attached to their surfaces ionic charges of a polarity opposite to that of the charged surface, adsorption of colloidal particles on the charged surface takes place until a complete monolayer of particles has been formed. When the monolayer is complete, the polarity of the surface has been reversed everywhere. The rate of this adsorption process depends on the concentration of the colloidal solution as well as on the particle size. The rate increases relatively weakly with the concentration and decreases heavily with increasing particle size. Since the colloidal particles have the same polarity, they are mutually repellant (so-called double layer repulsion), which counteracts the mutual van der Waals attraction so that aggregation of particles is prevented, and a uniform distribution of adsorbed particles on the surface is ensured.

The surface layer resulting from the adsorption of colloidal particles described above has thus attached ionic charges of a polarity opposite to that of the original charged surface. Consequently, a continued adsorption of the colloidal particles is prevented due to the repulsion between the monolayer of particles on the surface and the particles in the solution. By bringing the surface into contact with a solution containing colloidal particles having the opposite polarity in a new treatment step, it is possible to build up a further particle layer on the surface, thus again reversing the polarity of the charged surface. Such alternating exposures of the article to solutions containing colloidal particles having attached ionic charges of reverse polarity can be carried out until a surface layer of desired thickness is obtained.

A consequence of the process sequence described is that it is not necessary to know the polarity of the starting surface beforehand. If the surface is treated with a solution of colloidal particles having charges of the same polarity as those of the surface, adsorption will not take place due to the double layer repulsion effect, while adsorption will take place in the subsequent treatment, when the particles in the solution have charges of the opposite polarity.

Consequently, the method of the invention comprises contacting the charged surface with a fine-grained colloidal aqueous solution of a complex compound of heparin and a cationic surfactant, the colloidal particles having attached to their surfaces charges of a polarity opposite to that of the charges attached to the surface of the medical article. For certain purposes, a satisfactory heparinization can be obtained by a one-step treatment of the article with a colloidal solution of the type referred to above. It is preferred, however, that the treatment be repeated one or more times, after reversing the polarity of the charged surface to ensure complete coverage of the surface and a sufficiently thick film. This polarity reversal can take place by treating the surface, preferably after having rinsed it with water, with a colloidal solution which is of the type referred to above but in which the charged colloidal particles have a polarity opposite to that of the colloidal particles in the solution utilized in the first step. An alternative and simpler way of reversing the polarity is to expose the surface to an aqueous solution of the component of the complex compound which has an ionic charge of the opposite polarity to that of the particles in the colloidal solution used in the first step.

This means exposing the surface to an aqueous solution of heparin or a cationic surfactant, as the case may be.

We prefer to use a cationic surfactant of the primary amine type, and particularly an alkyl amine hydrochloride having 14-22, preferably 16-18, carbon atoms in the alkyl group. It is preferred that the primary amine surfactant has a critical micelle concentration ("CMC") of less than $5 \cdot 10^{-3}$ mol/liter. The critical micelle concentration is the lowest concentration at which micellar aggregates occur in an aqueous solution of a surfactant. More information on the CMC can be found in, for example, Mukerjee & Mysels: Critical Micelle Concentrations of Aqueous Surfactant Systems, issued by the U.S. National Bureau of Standards (NSRDS-NBS 36). We have found hexadecylamine hydrochloride (alternative name: cetylamine hydrochloride) to be a particularly useful cationic surfactant of the primary amine type.

The resulting surface is preferably stabilized by being treated with a dialdehyde, suitably glutardialdehyde, as disclosed in the Swedish Pat. No. 365.710. A large excess of heparin or cationic surfactant in the surface film can jeopardize the satisfactory result of the subsequent stabilizing treatment with dialdehyde. Therefore, it is preferred to wash the surface with pure water after the latest exposure to a colloidal solution of the complex compound of heparin and cationic surfactant, and subsequently treat the surface with a diluted aqueous solution of the component of the complex compound of which there is a deficiency in the colloidal solution used.

The stabilization process with a dialdehyde does not work satisfactorily if the complex compound has been formed by the reaction of heparin and a quaternary alkyl ammonium salt, such as cetyltrimethyl ammoniumbromide. Therefore, in this case the stabilization process should be preceded by a treatment of the surfac with a solution of a cationic surfactant of the primary amine type. An exchange reaction takes place, resulting in the formation of a complex compound between the heparin and said primary amine type surfactant, while the quaternary ammonium surfactant is removed from the surface. This is so because the solubility of the complex compound of heparin and the primary amine type surfactant is lower than that of the quaternary alkylammonium-heparin complex. When the exchange reaction is complete, the surface layer can be stabilized with a dialdehyde as disclosed.

Treatment of the surface with such solutions containing an excess of cationic surfactant, i.e. pure cationic surfactant solutions as well as colloidal solutions containing positively charged colloidal particles, should take place at a temperature exceeding the Krafft temperature of the cationic surfactant, whereas treatment of the surface with other solutions to advantage can take place at room temperature.

Treatment times of at most one or a few minutes are generally quite sufficient, when using pure heparin and cationic surfactant solutions as well as fine-grained solutions of the heparin-surfactant complex.

An important condition for obtaining sufficiently quick adsorption of colloidal particles on the surface, and thereby a short treatment time, and for obtaining complete coverage of a cohesive and fine-grained surface film of the heparin-surfactant complex, is that fine-grained colloidal solutions are used, meaning that the size of the colloidal particles is preferably less than 200 nm. It is also preferred that the colloidal particles have a size of more than 40 nm.

The invention also relates to a colloidal solution for carrying out the new heparinizing process. The solution is a fine-grained colloidal solution of a complex compound of heparin and a cationic surfactant, the heparin content being 1–100 I.U. mer ml, and the ratio of surfactant to heparin being such as to produce a light transmission of at least about 40% of that of pure water when the light wave length is 400 nm, the length of the optical passage is 1 cm, and the heparin content is 50 I.U. per ml, and to produce a light transmission of at least 90% of that of pure water when the light wave length is 400 nm, the length of the optical passage is 1 cm, and the heparin content is 10 I.U. per ml. Assuming that the relation between the lowest desired light transmission and the heparin content is substantially rectilinear, the lowest light transmission for other percentages can be found by interpolation or extrapolation.

To produce a fine-grained colloidal solution as defined above, it is important to avoid such conditions in mixing the two solutions which result in flocculation. If hexadecylamine hydrochloride is used as cationic surfactant, the flocculation point is at about $3.5 \cdot 10^{-5}$ mmol cationic surfactant per I.U. heparin. The flocculation points for other cationic surfactant such as tetra- and oktadecylamine hydrochloride, as well as cetyltrimethylammonium bromide can easily be determined by titration.

A fine-grained colloidal solution containing particles with positive charges attached to their surfaces can be produced in the following way: An aqueous solution of heparin with a heparin content of 1–100 I.U. per ml, preferably 10–60 I.U. per ml, is added successively under agitation to an aqueous solution of a cationic surfactant with a content of 0.5–50 mmol surfactant per liter preferably 3–30 mmol per liter, in such ratios that the amount of cationic surfactant exceeds, and suitably exceeds by at least 10%, the relative amount required for flocculation. A larger excess of the cationic surfactant than about 3 times in relation to the relative amount required for flocculation is less suitable, since it can create an unfavourably high content of Schiff's bases in the dialdehyde stabilized heparin surface. If hexadecylamine hydrochloride is used as surfactant, the amount of surfactant should be selected to be about $4 \cdot 10^{-5}$ to $10 \cdot 10^{-5}$ mmol per I.U. of heparin. The final content of heparin in the colloidal solution should be selected between 1 and 100 I.U. per ml, preferably 5–50 I.U. per ml. The pH of both solutions should be adjusted to between 2.5 and 7, while the temperature of the solutions should be selected higher than the Krafft temperature of the cationic surfactant, which for hexadecylamine hydrochloride is at about 48° C. The temperature is preferably below the boiling points of the solutions.

A fine-grained colloidal solution containing particles with attached negative charges attached to their surfaces can be produced in the following way: A solution of a cationic surfactant with a concentration of 0.01–10 mmol per liter is added successively under agitation to an aqueous solution of heparin with a heparin content of 5–500 I.U. per ml, such a quantity that the ratio between the cationic surfactant and the heparin is at most about 75% of the ratio required for flocculation. When using hexadecylamine hydrochloride as the cationic surfactant the quantity of surfactant should be at most about $2.7 \cdot 10^{-5}$ mmol surfactant per I.U. heparin. The temperature of the solutions should here also exceed the Krafft temperature of the cationic surfactant.

A simple and convenient way of determining whether the preparation of a colloidal solution of the heparin-surfactant complex has resulted in sufficiently small colloidal particles consists of measuring the light transmission of the colloidal solution in a spectrophotometer. We prefer to use a spectrophotometer operating with light having a wavelength of 400 nm, and with an optical passage having a length of 1 cm. If the light transmission of the colloidal solution exceeds 40% of that of pure water, when the heparin content of the colloidal solution is 50 I.U. per ml, and exceeds 90% of that of pure water when the heparin content of the colloidal solution is 10 I.U. per ml, the colloidal solution is sufficiently fine-grained to enable a short treatment time, viz. one or a few minutes. The lowest light transmission for other heparin percentages may be found by interpolation or extrapolation.

In the following Examples the measure of the effect of the heparinization process according to the invention is the trombocyte adhesion on a heparinized and stabilized surface in percent of the platelet adhesion on an untreated surface after exposure to citrated fresh whole blood. Incomplete coverage of the substrate surface by the heparin film usually results in a relative platelet adhesion clearly exceeding 10%. Examples 1–8 relate to the preparation of colloidal solutions, and Examples 9–24 relate to the heparinization of various medical articles with such colloidal solutions.

EXAMPLE 1

A fine-grained colloidal solution of heparin-surfactant particles having positive charges attached to their surfaces was produced according to the following. 125 ml of an aqueous solution containing 12 I.U. of heparin per ml was added under severe agitation to 25 ml of a 3 mmol/l aqueous solution of hexadecylamine hydrochloride. The pH of the solutions was adjusted to 3 before mixing, by adding HCl. The temperature of the solutions was 60° C. The heparin content of the colloidal solution was 10 I.U. per ml and the amount of hexadecylamine hydrochloride was $5 \cdot 10^{-5}$ mmol per I.U. of heparin. The light transmission of the solution for a wavelength of 400 nm and 1 cm optical passage was 90% of that of pure water.

EXAMPLE 2

A fine-grained colloidal solution of heparin-surfactant particles having negative charges attached to their surfaces was produced according to the following.

125 ml of a 0.24 mmol/l aqueous solution of hexadecylamine hydrochloride was added under severe agitation to 25 ml of an aqueous solution containing 60 I.U. heparin per ml. The temperature of the solutions was 60° C. The heparin content of the colloidal solution was 10 I.U. per ml and the amount of hexadecylamine hydrochloride was $2 \cdot 10^{-5}$ mmol per I.U. of heparin. The light transmission of the solution for a wavelength of 400 nm and 1 cm optical passage was 98% of that of pure water.

EXAMPLE 3

A fine-grained colloidal solution of heparin-surfactant particles having positive charges attached to their surfaces was produced according to the following.

125 ml of an aqueous solution containing 60 I.U. heparin per ml was added under heavy agitation to 25 ml of a 10 mmol/l aqueous solution of hexadecylamine hydrochloride. The pH of both solutions was adjusted to 3 before mixing, by adding HCl. The temperature of the solutions was 60° C. The heparin content of the colloidal solutions was 50 I.U. per ml and the amount of hexadecylamine hydrochloride was $6 \cdot 10^{-5}$ mmol per I.U. of heparin. The light transmission of the solution for a wavelength of 400 nm and 1 cm optical passage was 70% of that of pure water.

EXAMPLE 4

A fine-grained colloidal solution of heparin-surfactant particles having negative charges attached to their surfaces was produced according to the following.

125 ml of a 1.2 mmol/l aqueous solution of hexadecylamine hydrochloride was added under heavy agitation to 25 ml of an aqueous solution containing 300 I.U. heparin per ml. The temperature of the solutions was 60° C. The heparin content of the colloidal solution was 50 I.U. per ml and the amount of hexadecylamine hydrochloride participating was $2 \cdot 10^{-5}$ mmol per I.U. of heparin. The light transmission of the solution for a wavelength of 400 nm and 1 cm optical passage was 80% of that of pure water.

EXAMPLE 5

A fine-grained colloidal solution of heparin-surfactant particles having positive charges attached to their surfaces was produced according to the following.

125 ml of an aqueous solution containing 60 I.U. heparin per ml was added under severe agitation to 25 ml of a 12 mmol/l aqueous solution of hexadecylamine hydrochloride. The pH of both solutions was adjusted to 3 before mixing, by adding HCl. The temperature of the solutions was 60° C. The heparin content of the colloidal solution was 50 I.U. per ml and the amount of hexadecylamine hydrochloride was $4 \cdot 10^{-5}$ mmol per I.U. of heparin. The light transmission of the solution for a wavelength of 400 nm and 1 cm optical passage was 60% of that of pure water.

EXAMPLE 6

A fine-grained colloidal solution of heparin-surfactant particles having positive charges attached to their surfaces was produced according to the following.

125 ml of an aqueous solution containing 60 I.U. heparin per ml was added under heavy agitation to 25 ml of a 30 mmol/l aqueous solution of hexadecylamine hydrochloride. The pH of both solutions was adjusted to 3 before mixing, by adding HCl. The temperature of the solutions was 60° C. The heparin content of the colloidal solution was 50 I.U. per ml and the amount of hexadecylamine hydrochloride was $10 \cdot 10^{-5}$ mmol per I.U. of heparin. The light transmission of the solution for a wavelength of 400 nm and 1 cm optical passage was 60% of that of pure water.

EXAMPLE 7

A fine-grained colloidal solution of heparin-surfactant particles having positive charges attached to their surfaces was produced according to the following.

125 ml of an aqueous solution containing 12 I.U. heparin per ml was added under heavy agitation to 25 ml of a 6 mmol/l aqueous solution of cetyltrimetylammonium bromide. The pH of both solutions was adjusted to 3 before mixing, by adding HCl. The temperature of the solutions was 50° C. The heparin content of the colloidal solution was 10 I.U. per ml and the amount of cetyltrimethylammonium bromide was $10 \cdot 10^{-5}$ mmol per I.U. of heparin. The light transmission of the solution for a wavelength of 400 nm and 1 cm optical passage was 98% of that of pure water.

EXAMPLE 8

A fine-grained colloidal solution of heparin-surfactant particles having positive charges attached to their surfaces was produced according to the following.

180 ml of an aqueous solution containing 55.6 I.U. heparin per ml was added under heavy agitation to 20 ml of an aqueous solution containing 35 mmol/l hexadecylamine hydrochloride. The resulting pH was about 5. The temperature of the solutions was 60° C. The heparin content of the colloidal solution was 50 I.U. per ml, and the content of hexadecylamine hydrochloride was $7 \cdot 10^{-5}$ mmol per I.U. heparin. The light transmission of the solution for a wavelength of 400 nm and 1 cm optical passage was 45% of that of pure water.

EXAMPLE 9

Polyethylene catheters were exposed to a solution of potassium permanganate (2 g/l) in concentrated sulphuric acid for 2 minutes, whereafter they were washed with pure water. A first batch of catheters, thus oxidized, were exposed to the fine-grained colloidal solution, produced according to Example 1, for 15 seconds at 60° C., whereafter the catheters were washed with water at room temperature. They were subsequently exposed to an aqueous solution of heparin (10 I.U. per ml, pH 3) for some minutes at 60° C. This treatment sequence was terminated by washing with water. A second batch of catheters were exposed to two treatment sequences of the kind described. A third batch of catheters were exposed to three treatment sequences of the kind described. After terminated heparinization, the heparin film of all three batches of catheters was stabilized by treating the catheters with an aqueous solution of glutardialdehyde (0.5 percent by weight) for 20 minutes at 55° C. The catheters were finally well rinsed in pure water.

The treated catheters were now tested by exposure to citrated fresh whole blood for 20 minutes, and afterwards washed with 30 ml physiological common salt solution. The ATP-content of platelets having adhered to the surface of the catheters was extracted by using a tris-HCl-buffer and was determined by a chemical luminescense reaction with firefly extract. The following results were obtained:

| Number of treatment sequences | 1 | 2 | 3 |
|---|---|---|---|
| Platelet adhesion relative to untreated surface | 3.5% | 0.4% | 0.3% |

EXAMPLE 10

Polyethylene catheters were pretreated with potassium permanganate in the same way as in Example 9. A first batch of catheters were exposed to a fine-grained colloidal solution prepared according to Example 1, at 60° C. for 15 seconds, were rinsed with cold water, and were subsequently exposed to a colloidal solution prepared according to Example 2, at room temperature, for 15 seconds. This treatment sequence was terminated by washing with pure water. A second batch of catheters were exposed to two treatment sequences of the kind described. A third batch of catheters were exposed to three treatment sequences of the kind described. All catheters were stabilized and tested as stated in Example 9. The following results were obtained:

| Number of treatment sequences | 1 | 2 | 3 |
|---|---|---|---|
| Platelet adhesion relative to untreated surface | 3% | 0.3% | 0.4% |

EXAMPLE 11

Polyethylene catheters were first surface-oxidized for 30 minutes at a pressure of 1 Torr, by a gas mixture containing oxygen, monoatomic oxygen, ozone and singlet oxygen produced by a microwave discharge. A first batch of catheters were exposed to a fine-grained colloidal solution prepared according to Example 3, for 15 seconds, at 60° C. After having been washed with cold water, they were exposed to an aqueous solution of heparin (10 I.U. per ml, pH 3) for a few minutes at 60° C. This treatment sequence was terminated by washing with water. A second batch of catheters were exposed to two treatment sequences of the kind described. A third batch of catheters were exposed to three treatment sequences of the kind described. All catheters were stabilized and tested as set forth in Example 9. The following results were obtained:

| Number of treatment sequences | 1 | 2 | 3 |
|---|---|---|---|
| Platelet adhesion relative to untreated surface | 0.2% | 0.3% | 0.2% |

EXAMPLE 12

Polyethylene catheters were pretreated with potassium permanganate in the same way as in Example 9. They were now exposed for 15 seconds to a 1 mmol/l aqueous solution of hexadecylamine hydrochloride at 60° C., and were subsequently washed with water at room temperature. The catheters had now positive charges on their surfaces.

The catheters were now exposed to a colloidal solution prepared according to Example 4 for 15 seconds at room temperature, and after washing with water they were exposed to a 1 mmol/l aqueous solution of hexadecylamine hydrochloride for 15 seconds at 60° C. This treatment sequence was concluded by washing with water. The catheters were exposed to three such treatment sequences. The catheters were now stabilized and tested as stated in Example 9. The platelet adhesion relative to an untreated surface was found to be 0.5%.

EXAMPLE 13

Polyethylene catheters were pretreated with potassium permanganate in the same way as in Example 9. They were now exposed at room temperature for 1 minute with a fine-grained colloidal solution prepared according to Example 5. After washing with water they were stabilized and tested as described in Example 9. The platelet adhesion of the heparinized surface was found to be 3% of that of an untreated polyethylene surface.

EXAMPLE 14

The Example relates to the heparinization of vascular grafts, i.e. tubular articles used for making artificial blood-vessels. The vascular grafts of this Example consisted of Dacron web. They were first exposed for one minute to a fine-grained colloidal solution prepared according to Example 6. They were washed with cold water, and were exposed to an aqueous solution of heparin (20 I.U. per ml. pH 3) for five minutes at 60° C. This treatment sequence was concluded by washing with water, whereafter the whole treatment sequence was repeated two further times. Stabilizing treatment was carried out as described in Example 9.

Vascular grafts, both untreated and heparinized according to the above, were tested by exposure for 60 minutes in vitro to heparinized whole blood containing platelets labelled with radioactive isotopes. After terminated exposure, the grafts were washed with physiological common salt solution, and the amount of adhered platelets was determined by measuring the residual radioactivity. The platelet adhesion on the heparinized Dacron web amounted to about 10% of that of the untreated Dacron web.

EXAMPLE 15

Polystyrene test tubes were pretreated with concentrated sulfuric acid containing 2 g/l potassium permanganate for 10 minutes, whereafter they were well washed with water.

Test tubes, thus oxidized, were now exposed to a fine-grained colloidal solution prepared according to Example 3, for one minute, at 60° C. After having been washed with cold water they were treated with an aqueous solution of heparin (20 I.U. per ml, pH 3) for five minutes at 60° C. This treatment sequece was concluded by washing with water, whereafter the whole sequence was repeated two further times. Stabilizing treatment and testing was carried out as given in Example 9. The platelet adhesion on the heparinized polystyrene tubes amounted to 1% of the adhesion on the untreated polystyrene tubes.

EXAMPLE 16

Polyethylene catheters were pretreated with an aqueous solution containing 5% by weight of ammonium persulphate for two hours at 65° C. A first batch of catheters, thus oxidized, were exposed to a fine-grained colloidal solution prepared as disclosed in Example 8, for one minute at 60° C. They were now rinsed with water of room temperature, and were subsequently exposed to an aqueous solution containing 10 I.U. heparin per ml and having a pH of 3, for a few minutes at 60° C. They were finally rinsed with water. A second batch of catheters were exposed to two treatment sequences of the kind described. A third batch of catheters were exposed to three treatment sequences of the kind described. All catheters were stabilized and tested as has been disclosed in Example 9. The following results were obtained:

| Number of treatment sequences | 1 | 2 | 3 |
|---|---|---|---|
| Platelet adhesion relative to untreated surface | 10% | 0.5% | 0.5% |

EXAMPLE 17

Polyvinyl chloride catheters were pretreated first with a 1 M aqueous solution of hydrochloric acid and subsequently with an aqueous solution containing 5% by weight of ammonium persulphate for two hours at 60° C. The catheters were now exposed to a fine-grained colloidal solution prepared as disclosed in Example 8, for one minute at 60° C. They were now rinsed with water at room temperature, and were subsequently exposed to an aqueous solution containing 10 I.U. heparin per ml and having a pH of 3, for a few minutes at 60° C. They were finally rinsed with water. The treatment sequence described above was repeated twice. The catheters were now stabilized and tested as has been disclosed in Example 9. The platelet adhesion was found to be 1% of that of an untreated surface.

EXAMPLE 18

Cathethers of silicone rubber were pretreated first with an aqueous solution containing 1% albumin, for 30 minutes at room temperature, and subsequently with an aqueous solution containing 0.5% glutardialdehyde, for 15 minutes at room temperature. They were now exposed to a fine-grained colloidal solution prepared as disclosed in Example 8, for one minute at 60° C. They were now rinsed with water at room temperature, and were subsequently exposed to an aqueous solution containing 10 I.U. heparin per ml and having a pH of 3, for a few minutes at 60° C. They were finally rinsed with water. The treatment sequence described above was repeated twice. The catheters were stabilized and tested as disclosed in Example 9. The platelet adhesion was found to be 3% of that of an untreated surface.

EXAMPLE 19

Catheters of Teflon were pretreated first with an aqueous solution containing 1% albumin, for 30 minutes at room temperature, and subsequently with an aqueous solution containing 0.5% glutardialdehyde, for 15 minutes at room temperature. They were now exposed to a fine-grained colloidal solution prepared as disclosed in Example 8, for one minute at 60° C. They were now rinsed with water at room temperature, and were subsequently exposed to an aqueous solution containing 10 I.U. herparin per ml and having a pH of 3, for a few minutes at 60° C. They were finally rinsed with water. The treatment sequence described above was repeated twice. The catheters were stabilized and tested as has been disclosed in Example 9. The platelet adhesion was found to be 0.6% of that of an untreated surface.

EXAMPLE 20

Stainless steel plates (18/8-steel) were polished with abrasive paper, and were pickled with 1 M HCl. One batch (a) of plates were kept for reference, and one batch (b) was heparinized according to the following. The plates were first exposed to a fine-grained colloidal solution prepared according to Example 3, for one minute at 60° C. After having been washed with cold water they were exposed to an aqueous solution of heparin (10 I.U. per ml) for some minutes at 60° C. This treatment sequence was concluded by washing with water. The whole treatment sequence was repeated a further three times. Stabilizing treatment was carried out with 0.5% glutardialdehyde in water for 20 minutes at 55° C. The plates were finally washed carefully with water.

The plates of batches (a) and (b) were tested by exposure in rocking test tubes to citrated fresh whole blood for 20 minutes, whereafter they were washed with physiological common salt solution. The amount of adhered platelets was determined as described in Example 9. The adhesion of platelets on the heparinized steel plates amounted to 6% of the adhesion on the untreated plates. An examination of the surface with an Auger electron spectroscope disclosed that the steel surface was completely covered with a surface film consisting of the complex compound of heparin and hexadecylamine hydrochloride. No Fe or Cr signals could be detected.

EXAMPLE 21

Plates of stainless steel (Elgiloy) were pretreated with an aqueous solution containing 5% by weight of ammonium persulphate, for two hours at 65° C. They were now exposed to a fine-grained colloidal solution prepared as disclosed in Example 8, for one minute at 60° C. They were now rinsed with water at room temperature, and were subsequently exposed to an aqueous solution containing 10 I.U. heparin per ml and having a pH of 3, for a few minutes at 60° C. They were finally rinsed with water. The treatment sequence described above was repeated twice. The plates were stabilized and tested as described in Example 20. The platelet adhesion was found to be 0.4% of that of an untreated surface.

EXAMPLE 22

Test tubes of glass were pretreated first with an aqueous solution containing 1% albumin for 20 minutes, and subsequently, after having been rinsed with water, with an aqueous solution containing 0.5% glutardialdehyde for 15 minutes. The test tubes were now exposed to a fine-grained colloidal solution prepared as disclosed in Example 8 for one minute at 60° C., and were rinsed with water of room temperature. They were now exposed to an aqueous solution containing 10 I.U. heparin per ml and having a pH of 3, for a few minutes at 60° C. They were now rinsed with water. The treatment sequence now described was repeated twice. The test tubes were now stabilized and tested as disclosed in Example 9. The platelet adhesion was found to be 0.5% of that of an untreated test tube.

EXAMPLE 23

Circular plates of pyrolytic carbon to be used in an artificial heart valve having a diameter of 2.4 cm were pretreated by being exposed to concentrated sulphuric acid for one hour at room temperature. The plates were now exposed to a fine-grained colloidal solution prepared as disclosed in Example 8 for one minute at 60° C., and were subsequently rinsed with water of room temperature. They were now exposed to an aqueous solution containing 10 I.U. heparin per ml and 0.1 M NaCl, and having a pH of 3, for a few minutes at 60° C. They were now rinsed with water. The treatment sequence now described was repeated twice. The plates were stabilized and tested as described in Example 1. The platelet adhesion was found to be 1% of that of an untreated surface.

EXAMPLE 24

Polyethylene tubes were heparinized as described in Example 16, using three treatment sequences. The effect of the heparinization was tested in a patency test, in which compressed tubings were used as arterio-venous shunts on dogs. It was found that heparinized tubings remained patent during six hours without any reduction in the blood flow, and with no signs of platelet or coagulation activation. Untreated polyethylene tubings, however, were always totally occluded within 30 minutes due to platelet as well as coagulation activation.

What is claimed is:

1. A method of heparinizing a charged surface of a medical article intended for contact with blood, comprising contacting a charged surface thereof with a fine-grained colloidal aqueous solution of a complex compound of the components (i) heparin and (ii) a cationic surfactant, the particles of said colloidal solution having a size below 200 nm and having attached to their surfaces, charges of a polarity opposite to that of the charges attached to the surface of the medical article, the colloidal solution containing 1–100 I.U. of heparin per ml, the relative quantity of cationic surfactant in relation to the quantity of heparin being so adjusted that the light transmission of the colloidal solution at a wavelength of 400 nm and 1 cm optical passage exceeds about 40% of that pure water if the heparin content of the colloidal solution is 50 I.U. per ml, and exceeds about 90% of that of pure water if the heparin content of the colloidal solution is 10 I.U. per ml.

2. A method as claimed in claim 1, comprising subsequently contacting the medical article with a diluted aqueous solution of the component of the complex compound having an ionic charge the polarity of which is opposite to that of the colloidal particles and stabilizing the surface thus produced by contacting it with a dialdehyde.

3. A method as claimed in claim 1, comprising repeatedly contacting the article with the fine-grained colloidal aqueous solution with intermediate reversals of the polarity of the surface charge.

4. A method as claimed in claim 3 comprising reversing the polarity of the surface charge on the medical article by contacting the article with a second fine-grained colloidal aqueous solution of a complex compound of the components (i) heparin and (ii) a cationic surfactant, the particles of said colloidal solution having attached to their surfaces, charges of the same polarity as the charges on the original surface of the medical article.

5. A method as claimed in claim 3, comprising reversing the polarity of the surface charge on the medical article by contacting the article with an aqueous solution of the component of the complex compound having a charge of the same polarity as the charges on the original surface of the medical article.

6. A method as claimed in claim 1, for heparinizing a charged surface of a negative polarity on a medical article, comprising exposing the article to a finely dispersed colloidal aqueous solution of a complex compound of heparin and a cationic surfactant having a pH of between 2.5 and 7, and containing from about 1–100, I.U. of heparin per ml, and containing a relative quantity of cationic surfactant of at least about 1.1, and at most about 3 times, the relative amount of cationic surfactant required for flocculation of the complex compound, and subsequently exposing the article to an aqueous solution of heparin having a heparin content of 1–50 I.U. per ml.

7. A method as claimed in claim 1, in which the colloidal particles have a size above 40 nm.

8. A composition for the heparinization of a medical article by the method claimed in claim 1, consisting of a fine-grained colloidal aqueous solution of a complex compound of heparin and a cationic surfactant, the particles of said colloidal solution having a size below 200 nm, the colloidal particles having attached to their surfaces charges of positive or negative polarity, the colloidal solution containing 1–100 I.U. of heparin per ml, the relative quantity of cationic surfactant in relation to the quantity of heparin being so adjusted that the light transmission of the colloidal solution at a wavelength of 400 nm and 1 cm optical passage exceeds about 40% of that of pure water if the heparin content of the colloidal solution is 50 I.U. per ml, and exceeds about 90% of that of pure water if the heparin content of the colloidal solution is 10 I.U. per ml.

9. A composition as claimed in claim 8, in which the colloidal particles have attached to their surfaces charges with a positive polarity, the pH of the colloidal solution being between 2.5 and 7, the ratio between the quantities of cationic surfactant and heparin being at least about 1.1 and at most about 3 times greater than the corresponding quantity ratio at the flocculation point.

10. A composition as claimed in claim 8, in which the colloidal particles have attached to their surfaces charges with a negative polarity, the ratio between the quantities of cationic surfactant and heparin being lower than about 75% of the corresponding ratio at the flocculation point.

11. A method as claimed in claim 6, wherein the amount of heparin in the colloidal solution is from about 5 to 50 I.U. per ml.

* * * * *

UNITED STATES PATENT AND TRADEMARK OFFICE
CERTIFICATE OF CORRECTION

PATENT NO. : 4,265,927
DATED : May 5, 1981
INVENTOR(S) : Eriksson et al.

It is certified that error appears in the above—identified patent and that said Letters Patent is hereby corrected as shown below:

Cover Page, after Item [19], "Ericksson" should read --Eriksson--.
Cover Page, after Item [75], "Ericksson" should read --Eriksson--.
First Page, 3rd line of Abstract, "collodial" should read --colloidal--.
First Page, 5th line of Abstract, "collodial" should read --colloidal--.
Column 2, line 31, "articles" should be --particles--.
Column 4, line 38, "surfac" should be --surface--.
Column 5, line 7, "mer" should be --per--.
Column 11, line 20, "cathethers" should read --catheters--.
Column 11, line 47, "herparin" should read --heparin--.
Column 12, last line, "patency" should be --potency--.
Column 13, line 3, "patent" should be --potent--.
Column 13, line 23, after "that" insert --of--.

Signed and Sealed this

Eighteenth Day of August 1981

[SEAL]

*Attest:*

*Attesting Officer*

GERALD J. MOSSINGHOFF
*Commissioner of Patents and Trademarks*